United States Patent [19]

Rapach et al.

[11] Patent Number: 4,907,593
[45] Date of Patent: Mar. 13, 1990

[54] ADAPTATION OF HEART PACING TO PHYSICAL ACTIVITY

[75] Inventors: Charles M. Rapach, Clymer; David L. Purdy, Marion Center, both of Pa.; Orlando Maytin, Lauderdale Lakes, Fla.

[73] Assignee: Biocontrol Technology, Inc., Indiana, Pa.

[21] Appl. No.: 52,262

[22] Filed: May 21, 1987

[51] Int. Cl.⁴ .................. A61B 1/00; H05G 00/00
[52] U.S. Cl. ........................................ 128/419 PG
[58] Field of Search ............................. 128/419 PG

[56] References Cited

U.S. PATENT DOCUMENTS

| | | | |
|---|---|---|---|
| 3,593,718 | 7/1971 | Krasner et al. | 128/419 PG |
| 4,378,020 | 3/1983 | Nappholz et al. | 128/419 PG |
| 4,493,325 | 1/1985 | Hartlaub et al. | 128/419 PG |
| 4,549,548 | 10/1985 | Wittkampf et al. | 128/419 PG |
| 4,556,062 | 12/1985 | Grassi et al. | 128/419 PG |
| 4,624,260 | 11/1986 | Baker, Jr. et al. | 128/419 PG |
| 4,730,618 | 3/1988 | Lekholm et al. | 128/419 PG |
| 4,776,338 | 10/1988 | Lekholm et al. | 128/419 PG |

OTHER PUBLICATIONS

"Rate-Responsive Pacing: Biosensor Reliability and Physiological Sensitivity", PACE, vol. 10, May 1987.
"Trends in Pacemakers Which Physiologically Increase Rate: DDD and Rate Responsive", PACE, vol. 9, Nov-Dec. 1986.
"New Developments for Upper Rate Response in DDD Pacing", PACE, vol. 9, Nov.-Dec. 1986.
"Characteristics and Clinical Effects of Myopotential Signals in a Unipolar DDD Pacemaker Population", PACE, vol. 9, Nov.—Dec. 1986.

Primary Examiner—Kyle L. Howell
Assistant Examiner—Kennedy J. Schaetzle
Attorney, Agent, or Firm—Hymen Diamond

[57] ABSTRACT

A rate-changing implantable heart-stimulating device is disclosed, one that avoids use of moving parts and making unwanted rate changes. The device senses and responds to skeletal myopotential signals derived from the body of the wearer, preferably considering both amplitude and frequency of myopotential voltage signals which exceed a predetermined threshold value. The device preferably has two-way radio communication with an external programmer means.

20 Claims, 7 Drawing Sheets

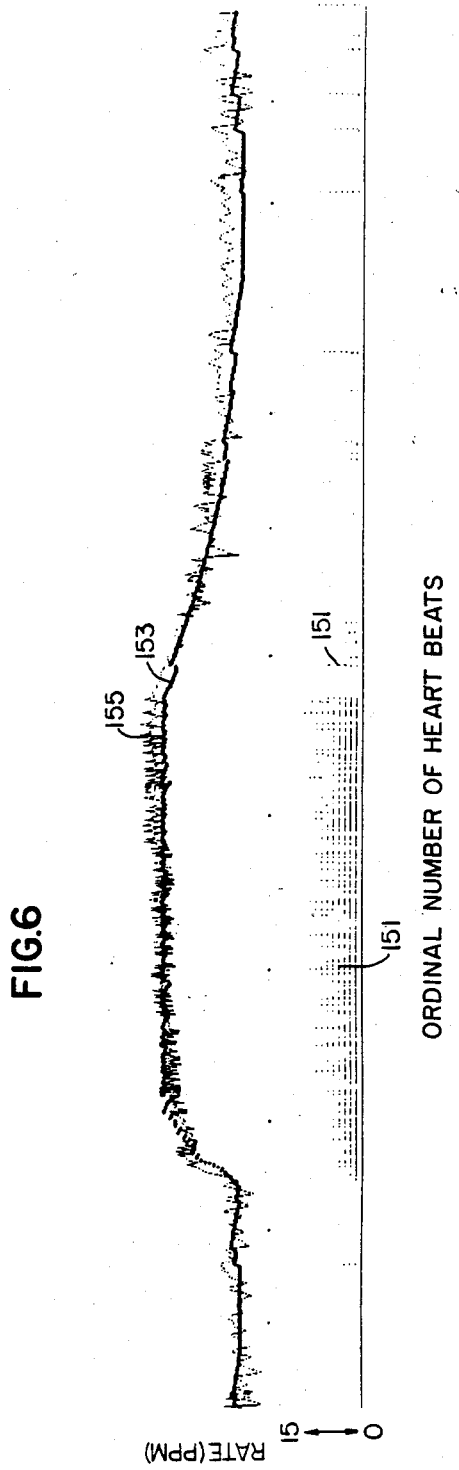

ADAPTATION OF HEART PACING TO PHYSICAL ACTIVITY

BACKGROUND OF THE INVENTION

This invention relates to the art of heart pacing and has particular relationship to heart pacing which is adapted to the physical activity of the host in whom a heart pacer is implanted. During physical activity the muscles absorb oxygen and glucose from the blood, generating carbon dioxide and producing other physiological and chemical changes in the blood. The pumping of the heart circulates the blood which supplies the oxygen and glucose, and the absorption of these components during physical activity is compensated in a person whose heart is operating normally by pumping of the heart at a higher rate and with an increase in stroke volume, thus pumping a greater volume flow rate of blood. The blood flow may increase by a multiple of between 3 and 5 as a result of increase in heart rate and only by a multiple of 1.3 to 1.5 in stroke volume as a result of increase. The increase in heart rate is therefore the predominant factor in the compensation. A pacemaker that directly senses muscular response during physical activity and increases the heart-beat rate accordingly would greatly increase the capacity of the host of the pacemaker for physical activity. It is an object of this invention to provide such a pacemaker.

The article entitled, *Research Leads to Major Breakthrough in Rate Responsive Pacemaking*, by Kenneth M. Anderson on pages 89 through 93 of *Medical Electronics* of Oct. 1986, describes a number of attempts at providing pacemaking whose rate is varied responsive to physical activity and lists some of their drawbacks. Kresh—*Facing Sensors for Heart- and Biophysical Telemetry*—35th ACBM Conference, and Kresh et al.—*Closed Loop Control of Heart Rate Basic Considerations*—AAIM 17th annual meeting, May 9–12, 1982, are also of interest. Anderson also describes in his paper briefly what he calls the "Activitrax" pacemaker which is described in more detail in his U.S. Pat. No. 4,428,378. An earlier pacemaker of the same type is described in Dahl, U.S. Pat. No. 4,140,132. Both of these pacemakers are alike in that in each case the body acceleration produced by the physical activity is imparted to a mass and converted into an electrical signal by a piezoelectric crystal. In Anderson the mass is the casing of the pacemaker; in Dahl, a lead block. In Anderson and Dahl, the pacer rate is not directly dependent upon the muscular response to physical activity. Both suffer from the disadvantage that what is essentially their accelerometers respond not only to the physical activity of the host in whom the pacemaker is implanted, but, also, to the acceleration and physical shocks to which the host may be subject overall, for example, in a vehicle moving on a rough or bumpy road or in driving a truck or a tractor or in any other vibrating structural body. Notwithstanding the statement in the right-hand column on page 92 of the Anderson article, the electrical signals produced by vigorous vibration of the host, which do not demand an increase in the pacing rate, may be substantial. The Anderson and Dahl pacemakers will also fail to respond to activity in situations in which an accelerometer is not responsive, as when the host is swimming.

In Gonzalez U.S. Pat. No. 4,201,219 the frequency of the pacemaker is modified by electrical signals detected in the nerve system relating to the control of the heart, i.e., to the cardiac contractions and lungs. Gonzalez's pacemaker is complicated by the supply of the neurosignals through a separate electrode in the pacemaker. In Krasner U.S. Pat. No. 3,593,718 the pulse rate of the pacemaker is varied in response to a physiological function such as the breathing rate. In this case also, the signal is supplied through a separate electrode.

It is an object of this invention to overcome the disadvantages and drawbacks of the prior art and to provide a method of variable-rate pacemaking in whose practice the rate shall be dependent on substantially any and all physical activity of the host in whom the pacemaker is implanted, but substantially only on such physical activity and not on the vibrations and shocks which the host as a whole undergoes. It is also an object of this invention to provide a pacemaker for practicing this method.

SUMMARY OF THE INVENTION

This invention arises from the realization that the myopotential, i.e., the potential developed across the cells of the muscles of the host during physical activity is a direct consequence of all physical activity and can serve to stimulate and regulate the pacing system. Myopotential is not developed when the host drives a truck or a tractor or rides on a rough road. It is developed by physical activity such as when the host is swimming. The myopotential is sometimes referred to herein as the skeletal potential or skeletal signal since it is derived mostly from the skeletal muscles of the host's body. The myopotential should be distinguished from the nerve potential. The nerve signal is derived from the nerves. The myopotential swings between peaks and valleys at a frequency typically predominantly of between 30 and 60 Hertz and the amplitude of the swings and their frequency is dependent on the vigor of the physical activity. The more vigorous the activity, the higher the amplitude and the frequency.

In accordance with this invention, the myopotential signal is sensed and the pacing rate of the pacemaker is adjusted or varied in accordance with the myopotential parameter derived from this sensing. The use of myopotential has the advantage that it is a direct measure of the physical activity of the host and is not substantially affected by the vibrations and shocks which the host as a whole may undergo. In addition, the process of controlling the pacing is purely electrical and does not involve mechanical components as in Dahl and Anderson.

In addition to sensing, in the practice of this invention, the skeletal muscle signals, such as the pectoralis major and minor muscles, which move the arm forwardly, or the latissimus dorsi muscle, which moves the arm rearwardly, to derive a parameter for adjusting pacing rate, the diaphragm muscle, which causes breathing, is monitored. This diaphragm muscle increases its signal with exercise since the breathing rate increases with exercise to increase the oxygen flow to the lungs and the $CO_2$ release from the lungs. It also increases its signal if breathing rate increases for other reasons, such as in a fight or in flight response, or the administration of epinephrin. This invention then also comprehends within its scope the concept of feedback through the medium of increased breathing rate, as well as through skeletal muscle movement. The sensing mechanism in the practice of this invention, of course, senses both breathing muscle and skeletal muscle signals simultaneously. There is some lag in the response to breathing, since skeletal muscle motion precedes diaphragmatic muscle increase in motion.

The use of the myopotential constitutes a radical departure from current prior-art practice. In prior-art pacemakers, the myopotential is suppressed. See, for example, *The Clinical Incidence and Significance of Myopotential Sensing With Unipolar Pacemakers*—Fetter, Bobeldyk and Engman—*PACE*—Sept.-Oct., 1984, Part V, Vol. 7, pages 871-881; and see, also, the two articles, *Preventing Myopotential Inhibition of the Unipolar Demand Pacer*—Wickham, pages 340-343, and *Biological Signals and Their Characteristics as a Cause of Pacemaker Malfunction*—Ohm, Hammer, Morkrid, pages 401-404, both in *Cardiac Pacing—Proceedings of the Fifth International Symposium on Cardiac Pacing*—Tokyo, 1976—Wanatabe, Toshio—Editors.

The human body is an electrical conductor having moderate resistance of the order of about several hundred ohms. During physical activity, the potential is impressed across the body between terminals, and the current flows in the same manner as it would flow over a resistant sheet or web between whose ends potential is impressed spreading out laterally along the sheet and converging at the poles of the potential source. An implanted heart pacer taps the potential drop across the portion of the body resistance between its electrode and the casing of the pacemaker. The resistance between the electrode tip and casing is of the order of 500 ohms. Compared to this resistance, the resistance through the pacemaker between the electrode and the casing, which is of the order of 30 thousand ohms, is effectively an open circuit.

In arriving at this invention, it has been realized that the difference between the amplitude of the heart pulse which is generated by the pacemaker or produced naturally by the heart and the amplitude of the myopotential drop between the electrode and the casing of the pacemaker is so great, that each of these parameters can perform its function independently of, and without interference from, the other. The pacemaker supplies a pulse to compensate for an absent R-wave, a wave of a type which, if present, would stimulate a contraction of the heart muscle. The R-wave, whether natural or simulated by the pacemaker, typically has an amplitude of about four or five millivolts. The myopotential drop across the electrode and casing is typically less than one millivolt.

In the practice of this invention, a pacemaker is provided which includes a microcomputer for producing the heart pulses and timing the interval between successive pulses and other intervals. The main operating program is stored in the read-only memory of the microcomputer; the timing and mode parameters are stored in its random-access memory and lend themselves to ready alteration through a remote programmer.

Typically the pacemaker is designed to condition the delivery of 70 pulses per minute during standby; i.e., when the host is substantially physically inactive. The duration between pulses is then about 857 milliseconds. Following the generation of a pacer or heart pulse, the pacemaker sensing is disabled during a refractory subinterval whose duration is typically about 300 milliseconds. Following the refractory subinterval there is a subinterval typically of maximum duration of about 557 milliseconds which is called the escape subinterval. The escape subinterval is terminated by a pacemaker or heart pulse which starts a succeeding refractory subinterval. The pacemaker rate is controlled in the practice of this invention by setting the duration of the escape subinterval, responsive to the myopotential, between the maximum duration of typically 557 milliseconds and a selected minimum duration which determines the maximum pacing rate. For a maximum pacing rate of 150 pulses per minute, and with a refractory subinterval of 300 milliseconds, the escape interval is 100 milliseconds. The microcomputer times a sampling interval during the refractory subinterval, typically about 100 milliseconds in duration, during which the myopotential signal is received and evaluated. The sampling interval typically occurs during the last 100 milliseconds of the refractory subinterval, but may occur at other points in the cycle.

Between the pacemaker electrode and the microcomputer, a plurality of independent channels are connected. These include a channel for transmitting intelligence of the occurrence of a natural heart pulse to the computer, a channel for transmitting a pacemaker pulse from the computer to the electrode (in the absence of a heart pulse) and a channel for transmitting myopotential signals to the computer. The channel which transmits the intelligence of the occurrence of heart pulse has a threshold of about three millivolts, so that it does not transmit the myopotential signals. The channel which transmits the myopotential signals has a threshold of about 0.1 to 1.0 millivolts. Since the myopotential channel is open only during a controlled sampling interval of the pacemaker cycle, heart pulses do not flow prematurely through this channel. Preferably, the interval during which this channel is open is at the end of the refractory subinterval, but it may occur in other parts of the pacing cycle.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which:

FIG. 6 is a graph demonstrating in waveforms a and b the performance of a prototype pacemaker in accordance with this invention.

DETAILED DESCRIPTION OF EMBODIMENT

Figure 1:
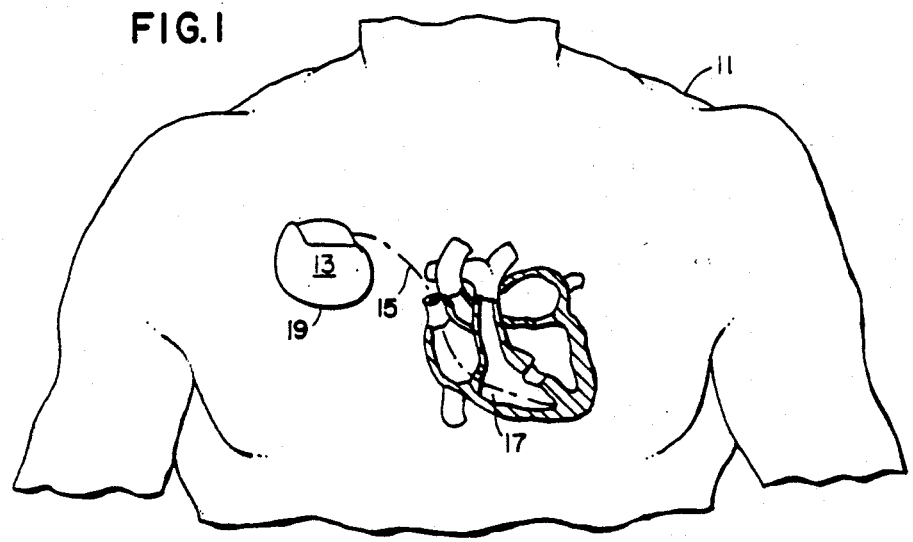
FIG. 1 is a diagrammatic view showing the rudimentary features of this invention.

FIG. 1 shows the upper part of the torso of a host 11. The pacemaker 13 is implanted in the chest of the host 11. The electrode 15 extends to the ventricle 17. The myopotential voltage which controls the pacing is tapped between the electrode 15 and the casing 19 of the pacemaker 13.

Figure 2:
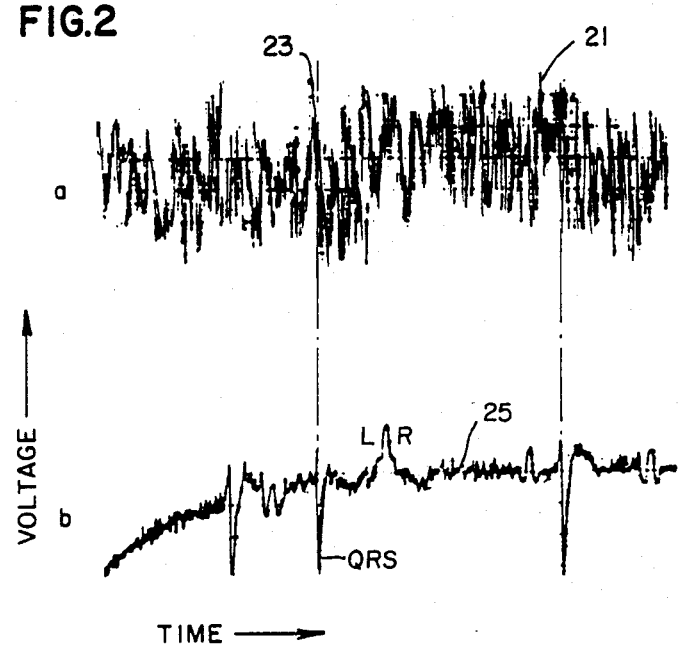
FIG. 2 is a graphical presentation showing in graph a typical myopotential pulses and in graph b the related accompanying heart pulses.

In FIG. 2, time is plotted horizontally and voltage vertically. The time axis is common to both graph a and graph b, i.e., lines parallel to the voltage axis represent the same instant of time in graph a and graph b. Graph a presents the myopotential produced between electrodes at the extremities of the host. The myopotential pulses 21 have nearly the same amplitudes as the heart pulses 23. Graph b presents the myopotential pulses 25 impressed between the electrode 15 and the casing 19. The amplitude of these pulses 25 is substantially smaller than the amplitude of the heart pulses 23. The overall period of time represented by FIG. 2 is of the order of 3.7 seconds.

Figure 2A:
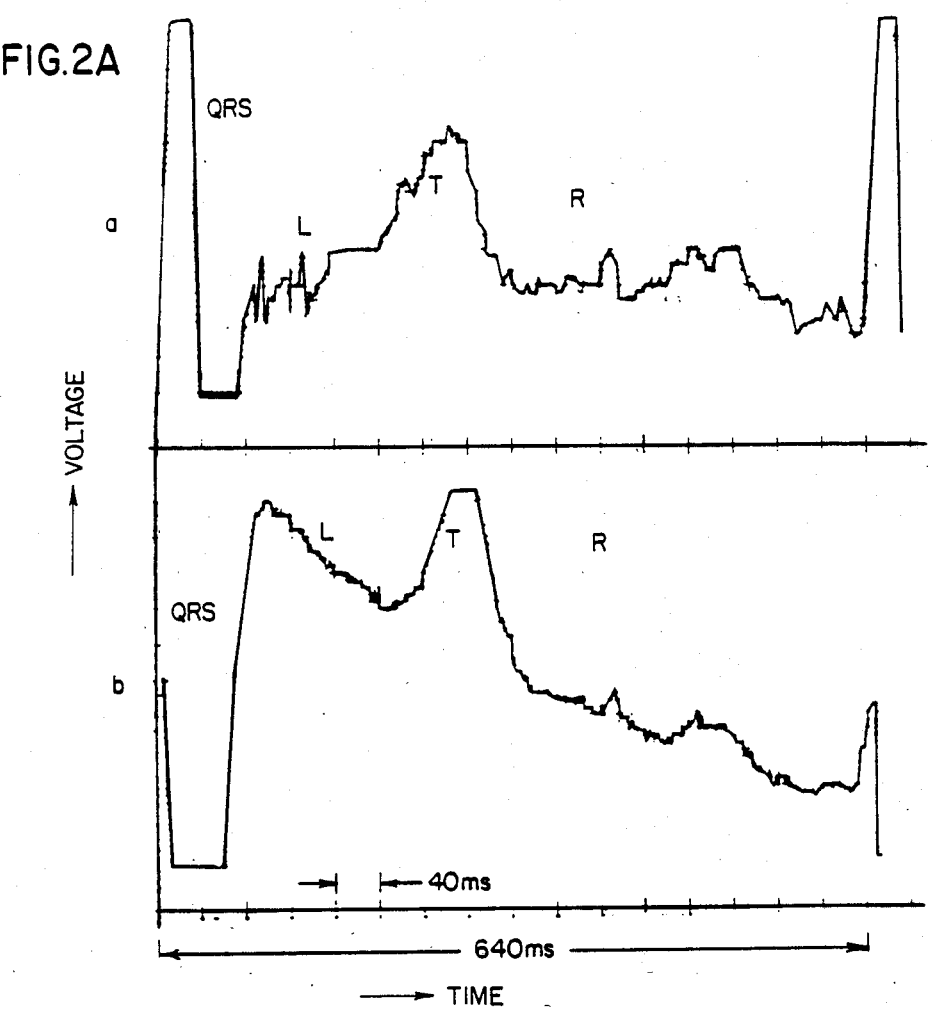
FIG. 2A is a graphical presentation similar to FIG. 2 produced with a host in whom an electrode was implanted and showing myopotential signals in graph a and the related accompanying heart pulses in graph b.

In FIG. 2A, graph a shows one cycle of potential derived between a surface electrode in contact with the upper chest on the right, where a pacemaker would normally be implanted, and a surface electrode in contact with the chest on the left near the bottom of the heart where the heart electrode would normally be implanted. The QRS and T pulses of the heart are labeled. In FIG. 2A graph b is the simultaneous one cycle of potential between an electrode implanted in the heart and a subcutaneous needle in the upper chest on the right where a pacemaker would normally be implanted. The host was exercising. The peaks and valleys on each side L and R of the wave show the myopotential signals. As shown in FIG. 3A, a pacing cycle starts with a natural or a stimulated R-pulse. Immediately following the R-pulse, there is a refractory subinterval during which the pacemaker sensing is disabled. This refractory subinterval is followed by an escape interval during which the pacemaker sensing is enabled. The escape interval is terminated, and a new refractory subinterval starts, either if, after a predetermined subinterval, there is a pacer pulse or if a natural R-pulse occurs before the end of this subinterval. A sampling subinterval during which the pacemaker is enabled to receive myopotential pulses occurs near the end of the refractory subinterval. This time interval is labeled "Variable Skeletal Sampling Time" in FIG. 3A.

Figure 3:
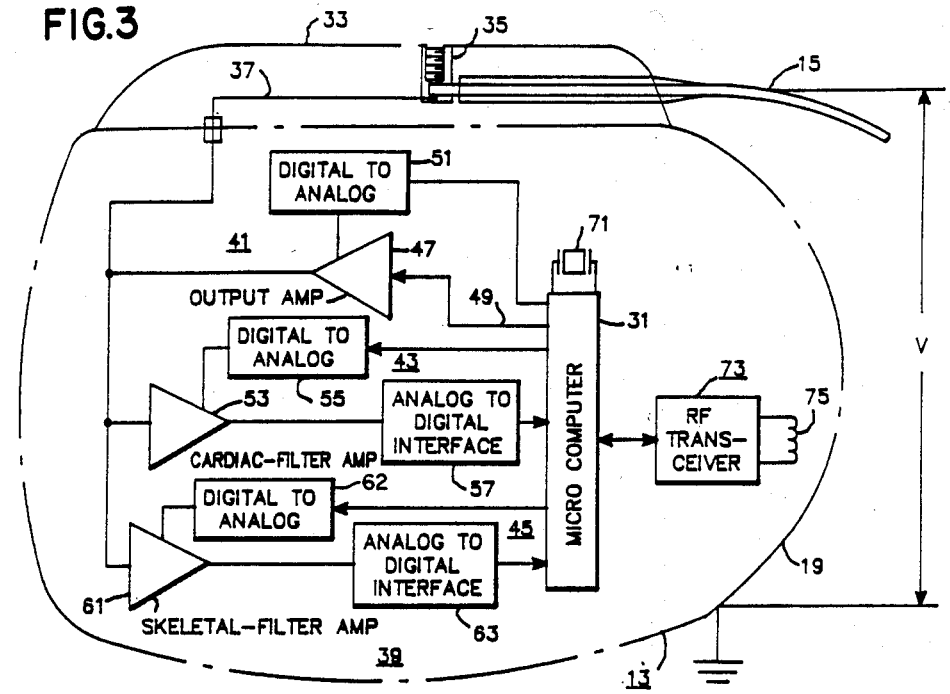
FIG. 3 is a block diagram partly schematic showing a heart pacemaker in accordance with this invention for practicing the method of this invention.
Figure 3A:
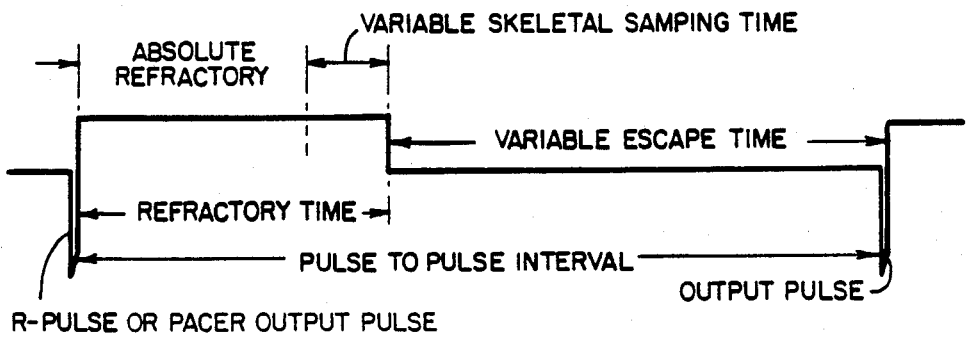
FIG. 3A is a diagram showing a typical pacing cycle including the myopotential sampling interval.

The pacemaker 13 includes, within the casing 19, a microcomputer 31 (FIG. 3). The casing 19 has a top 33 of EPOXY resin or the like. Within the top 33, a lead or electrode-connector block 35 is embedded. The electrode 15 is connected by the connector block 35 to the input network 39 of the microcomputer 31 through the input connector 37. The portion of the electrode 15 terminating in the pacemaker and the input conductor 37 are embedded in the top 33.

The input network 39 includes a plurality of channels 41, 43 and 45, each connected independently of the other, between the conductor 37 and the computer 31. Channel 41 includes an output operational amplifier 47 connected to transmit heart pulses, generated as numbers in the microcomputer 31, through the electrode 15 to the heart 17. The computer 31 is programmed to deliver a signal through conductor 49 to enable the output pulse to pass through the output amplifier 47. The digital-to-analog converter 51 converts the numbers at the output of the computer 31 to set the analog amplitude of the output pulse to be delivered to the heart through conductor 37 and electrode 15.

The channel 43 includes the amplifier 53, which conducts the voltage indications of a pulse from the heart to the microcomputer 31. The amplifier 53 is enabled at the beginning of the escape subinterval, by digital signals from the computer 31 which are converted into analog signals by digital-to-analog converter 55. The pulse from the heart produces at the output of amplifier 53 analog signals which are converted by analog-to-digital interface 57 into numbers.

Channel 45 includes operational amplifier 61. At the variable skeletal beginning of the sampling time or during the refractory subinterval, the amplifier 61 is enabled by a signal from the computer 31 derived through digital-to-analog converter 62. The amplifier 61 transmits myopotential signals to the microcomputer 31 through analog-to-digital interface 63. The amplifier 61 has a pass band optimized for myopotential-signal sensing; the band is between 30 Hertz and 60 Hertz.

The pacemaker 13 also includes a crystal oscillator 71. The oscillator 71 is connected to operate as a clock for the computer. Typically the crystal operates at a frequency of 32,768 Hertz.

The pacemaker 13 also includes a radio-frequency transmitter-receiver 73 which is connected to the computer 31 to enable an external programmer to program the computer. The transmitter-receiver includes an input-output coil 75, through which the programmer can communicate with the computer. Typically, the transmitter-receiver operates at a frequency of 32,768 Hertz.

Figure 4:
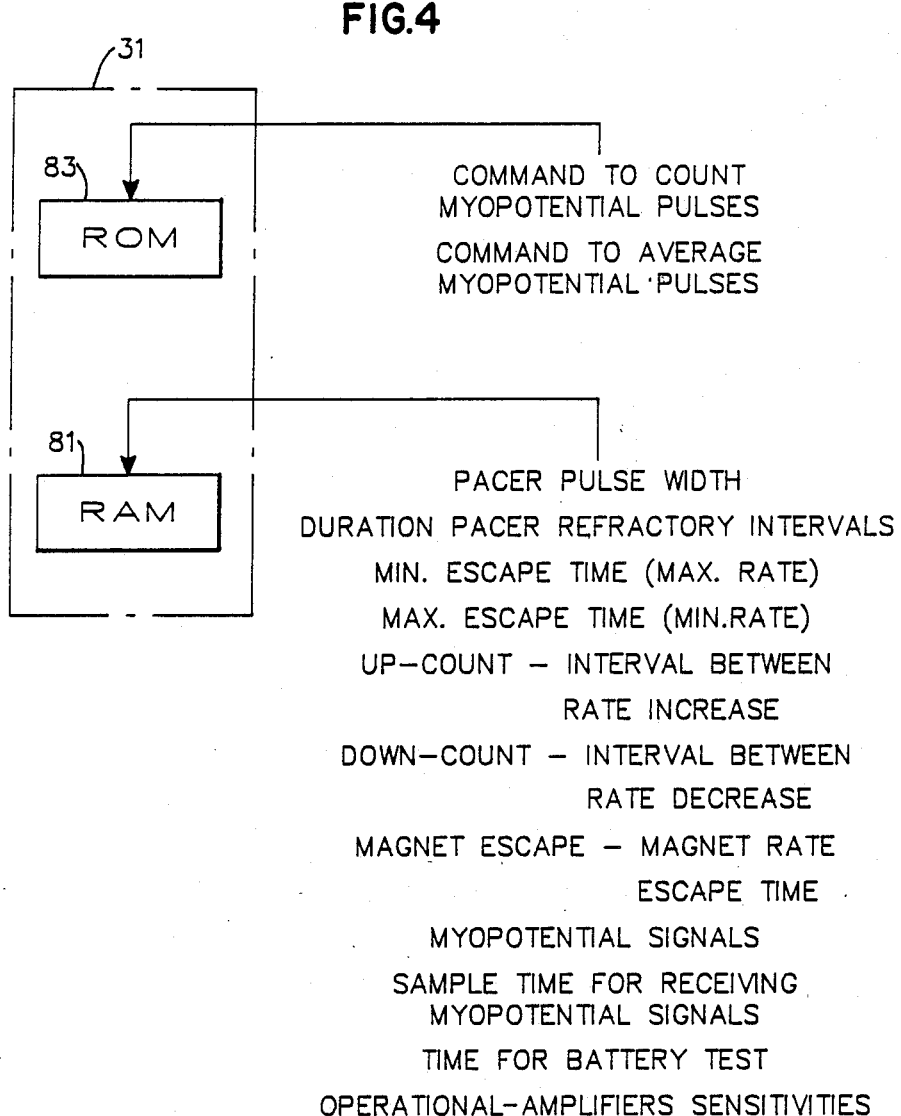
FIG. 4 is a block diagram illustrating a function of the microcomputer of the pacemaker shown in FIG. 3.

Referring now to FIG. 4, the random-access memory (RAM) 81 and the read-only memory (ROM) 83 are part of an integrated assembly of bits in the microcomputer 31. But in FIG. 4, the RAM and the ROM are shown as separate blocks, to facilitate the understanding of this invention. FIG. 4 shows the more significant items of intelligence which are stored in each memory. The intelligence in the RAM is stored and changed as necessary by an external programmer means through the transmitter-receiver 73. The intelligence is impressed electromagnetically through the coil 75. The ROM contains the fixed operational commands.

Physical activity is detected by amplifying and processing the myopotential (or skeletal-muscle) signals. When the skeletal signal exceeds a certain threshold, indicating that the host is currently engaged in such substantial physical activity as to make it advisable to cause some change in the pulse rate, the microprocessor 31 operates according to the program stored in ROM 83 and the variables in RAM 81 to increase slowly the pacing rate so that the heart may pump more blood to meet the host's body's increased energy requirements. The rate of increase and the upper rate limit and the rate of decrease and the lower limit are selectable parameters in the RAM 81. When skeletal or myopotential signals are no longer sensed, this indicating a decrease in or a lack of physical activity, the microprocessor 31 slowly decreases the pacing rate until it reaches the programmed lower limit. The rate of decrease may be different than the rate of increase, and preferably, it usually is, being slower, to match the usual functioning of the human body. It may be desirable to maintain an increased heart rate for some short period of time after activity is no longer sensed (i.e., the myopotential signals are no longer being passed) to allow the body to recover from the activity. The existing pacing lead or electrode 15 is used to sense skeletal signals; therefore, no external sensor is required. The vibrating component of Dahl or Anderson is eliminated. In the practice of this invention, the control is electrical; moving parts are dispensed with.

To revert to FIG. 3, a separate amplifier 61 in a signal processing channel 45 is integrated into the pacer circuit to detect the skeletal signals independently of the normal cardiac waveform sensing channel 43. The skeletal sensing amplifier 61 is designed for optimal sensing of the skeletal or myopotential signals.

The rate limits and other parameters related to the rate-change algorithm, as well as other usual pacing parameters are stored in the RAM 81 of the microcomputer's memory. This information is transmitted to the pacer from the external programmer by way of the RF communication link 73. Thus, the response of the pacer 13 can be adjusted over a wide range to meet individual requirements, and this can be done before, during, or after implant.

The concept here disclosed of sensing physical activity by means of myopotential signals may be extended to dual-chambered pacing by adding the skeletal-sensing circuitry and rate-change algorithm to a dual-chamber circuit. In a patient with a functional, but unresponsive atrial chamber, A-V (atrial-ventricular) synchrony could be maintained, as well as adding rate response to physical activity.

The rate of the change in the pulse interval set by the pacemaker is programmable. When the activity threshold is reached, the escape subinterval (FIG. 3A) is shortened by (X) milliseconds every (Y) pacemaker intervals until the upper rate limit is reached. If activity is no longer detected, the escape subinterval is lengthened (W) milliseconds every (Z) pacemaker intervals until the lower limit of pulse rate is reached.

Sensing skeletal activity in the host is defined as occurring when the amplitude of the skeletal or myopotential signal exceeds a voltage threshold level and/or when the amplitude exceeds a voltage threshold level a number of times in a sample interval. These levels are programmable. The parameter which measures the magnitude of the change in the escape subinterval may be evaluated in several ways, typified by the following: The number of myopotential signals which extend a threshold during each sampling subinterval may be counted. The average of the amplitudes of the myopotential signals which exceed a threshold during each sampling subinterval may be computed. The average number of myopotential signals which exceed a threshold, averaged over several successive sampling subintervals, may be computed.

The pacemaker 13 may be set to operate in a number of different modes, typified by the following:

Signal-test mode. This serves to aid in programming the activity threshold. When the equipment is activated by the external programmer means, an indication is given on the programmer when skeletal signals are sensed. The physician may quickly verify that the pacemaker's activity sensing is set properly.

Off/on mode. When the set activity is reached (skeletal signals exceed a certain amplitude and/or number of transitions), the pacing rate is sloped upwardly at the programmed increment until the upper rate limit is reached. When activity is no longer detected, the pacing rate is sloped downwardly until the lower rate limit is reached.

Sampling mode. To avoid interference from normal cardiac signals and the pacer's own output, the microcomputer 31 enables the skeletal sensing amplifier 61 only during certain times in the pacing cycle. Since skeletal signals are present over the entire pacing cycle, while cardiac signals are normally present over a predictable portion of the cycle, this selection of intervals during which the pacer's own signals are absent is feasible. This sampling time is programmable both in location in the refactory survival of the pacemaker cycle and also in length.

Proportional mode. The percentage of time the skeletal sensing threshold is exceeded during successive sampling intervals is measured and the rate is adjusted proportionately. The rate of increase of the pacing rate to the adjusted pacing rate and the rate of decrease from the adjusted pacing rate at the end of the physical activity are set at predetermined rates of change. If the activity level is gauged at 50% by this practice, the rate is only increased by one-half of the difference between the lower and upper limit instead of being increased to the maximum programmed limit while the physical activity is continued.

Interference rejection. Signal-processing techniques are used to ensure that outside interference is not mistaken for skeletal signals. If the frequency of occurrence of skeletal signals exceeds a predetermined number in a sample period, the signal is assumed to have a noise origin and be not related to physical activity. Successive signal samples are compared and if they continue to be identical, the source of the signals is identified as outside noise interference rather than the desired skeletal signals which constantly change.

Figure 5A:
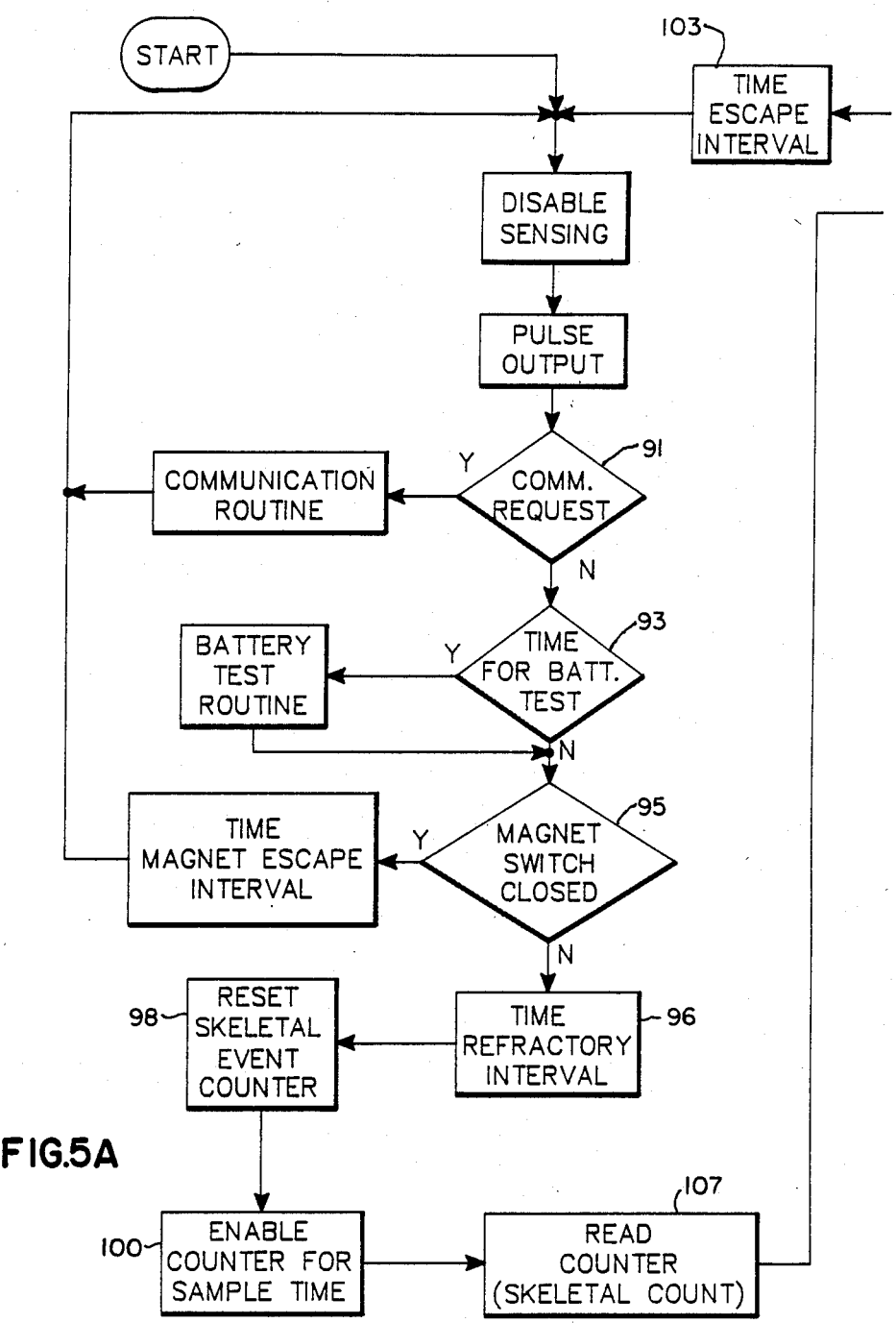
FIGS. 5A and 5B together are an algorithm of the operation of the pacemaker shown in FIG. 3.
Figure 5B:
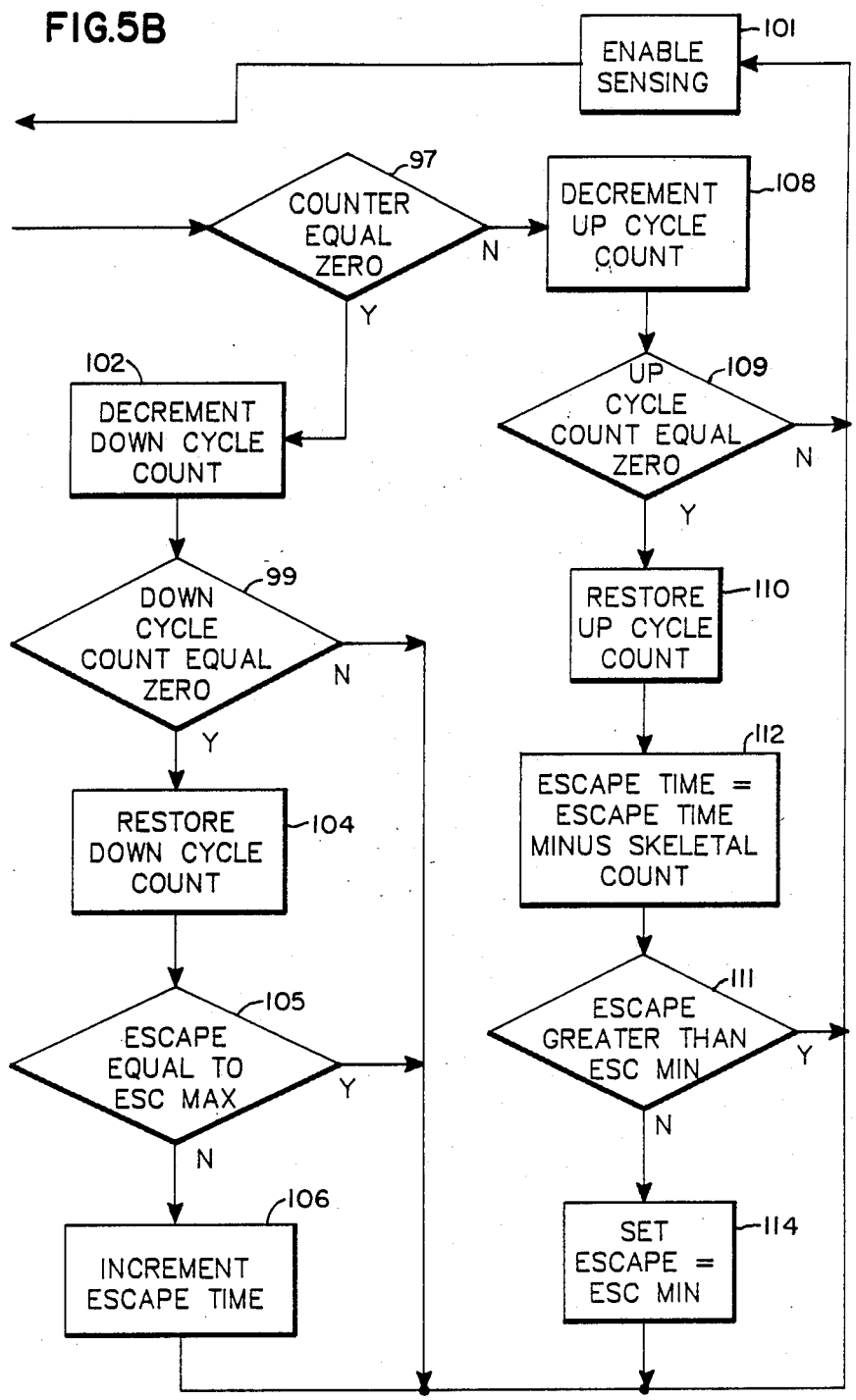

The operation of the pacemaker 13 is shown in the algorithm in FIGS. 5A and 5B. The microcomputer 31 is programmed to carry out the steps of the algorithm automatically. At the "START" of an operation, sensing is disabled and the pacemaker 13 operates in the normal pulse mode. The transmitter-receiver 73 is interrogated (diamond 91) to determine if there is intelligence from the outside programmer. If there is, the outside program is performed, and the pacemaker 13 is reset to "START". If not, there is interrogation (diamond 93) if the time for battery test has arrived. If it has, the battery test routine is carried out. If it has not, or after the battery test, there is interrogation (diamond 95) if the magnet switch is closed. If it is, the magnet escape subinterval is timed and the operation is returned to "START". No sensing occurs during magnet operation. The operation continues to cycle from "START" back to "START" until the magnet switch opens.

If, or after, the magnet switch is open, the refractory subinterval (block 96) is timed, the myopotential-event (skeletal event) counter (in microcomputer 31) is reset, this counter is then enabled (block 100) during the sampling interval, and this counter is read to (block 101) determine the count of myopotential events. The myopotential-event counter 107 is interrogated (diamond 97) to determine if the count is or is not 0. If this count equals zero (no physical activity), the down-counter cycle is decremented (block 102). The down-counter cycle is the number of cycles which are counted before the escape subinterval is incremented. This operation assumes that there may have been physical activity which has just stopped. The down-cycle counter is interrogated (diamond 99). If the down-cycle count is not zero, the sensing for a natural pulse is enabled (block 101), the escape subinterval is timed (block 103), and another operation is started.

If the down-cycle count is zero, which means that any activity which in the past has caused an increase in the rate of the pacemaker has terminated and that the decay from this increase has terminated, the down-cycle count is restored (block 104), and there is interrogation (diamond 105) to determine if the escape subinterval is a maximum. If it is, the sensing is enabled and the escape subinterval is timed in accordance with the new sensing. Then the operation is returned to "START". If the escape subinterval is not equal to the escape subinterval maximum, the escape subinterval is incremented (block 106), the sensing is enabled, and a new escape subinterval is timed.

If the decision (diamond 97) which monitors the state of the myopotential or skeletal count (block 107) determines that the myopotential count is not zero; i.e., patient is physically active, the up-cycle count is decremented (block 108), and there is interrogation (diamond 109) of the up-cycle count. The up-cycle count is the number of cycles of the pacemaker which are counted before the escape subinterval is decremented to increase the pacing frequency. If the up-cycle count is not zero, the sensing is enabled, and a new escape time subinterval is established. Then the operation returns to "START". If the up-cycle count is zero, the up-cycle count is restored (block 110), then the escape subinterval is set (block 112) to the shortened duration determined by the myopotential count (block 112) and there is interrogation (diamond 111) to determine if the new duration of the escape subinterval is greater than the minimum. If it is, the sensing is again enabled and the next escape subinterval set. Then the operation returns to "START". Each new escape subinterval is identified in FIG. 5B. as "N ESCAPE TIME" to distinguish it from the preceding subinterval. If the escape-subinterval duration is not greater than the minimum duration, the escape subinterval is set to minimum duration (block 114), the sensing is enabled, and a new escape subinterval is reset, and the operation returns to "START". The setting of the new escape time by subtracting the number of skeletal (myopotential) events from the old escape time is a convenient way of adjusting the escape time to accommodate physical activity. Since the escape time and the number of skeletal events are both numbers, the new escape time is a number which is coordinated with the number of skeletal events.

In producing graphs a and b of FIG. 6, one of the instant inventors engaged in physical activity climbing up and down a ladder with the electrodes of an EKG attached to his body approximately where the electrode 15 and casing 19 of pacemaker 13 would be contacted. A magnetic tape of the myopotential and heart signals of the inventor was produced. The output of the tape was impressed on a bread-board prototype embodying this invention and graphs a and b of FIG. 6 were produced. The activities indicated in graphs a and b of FIG. 6 took place over a period of time of approximately 12 minutes.

In graph b of FIG. 6 the ordinal numbers of the heart beats, starting with 1 for the first on the left, is plotted along the horizontal axis and the numbers of myopotential pulses occurring during each heart beat are represented by dots or bars 151 which extend vertically above the point corresponding to each numbered beat. In graph a of FIG. 6 the same ordinal number of heart beats is plotted horizontally and pacing rate vertically.

The heavy line 153 is a plot of the pacer rate as a function of time and the lighter jagged line 155 is a plot of the heart rate of the inventor who engaged in the physical activity as a function of time. Graphs a and b are coordinated. Each set of vertical dots or bars is vertically aligned with the heart beat to which it corresponds, i.e., the points along the horizontal axes of graphs a and b which are at the intersection of the same vertical line represent the same ordinal heart-beat number. Graph a shows that the pacer frequency increases and decreases corresponding to the physical activity as manifested by the heart rate signals.

Figure 7:
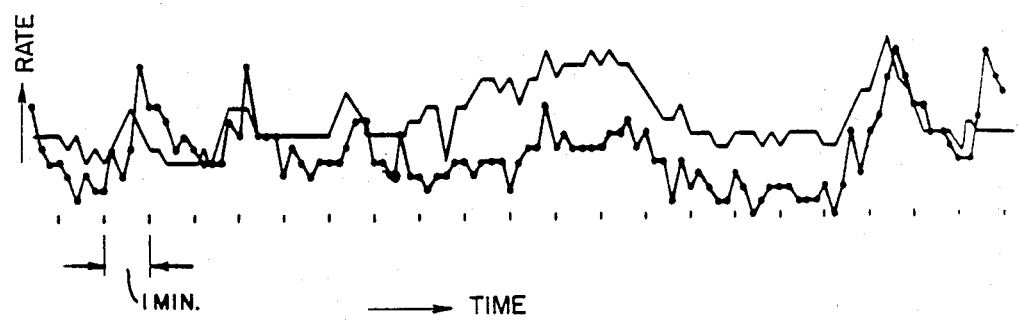
FIG. 7 is a graph produced with an electrode implanted in a host.

FIG. 7 is a reproduction of a tape produced with an electrode implanted in the heart of a host and the pacemaker external to the host. The host was supine on a table and intermittently peddled bicycle wheels while moving her left arm. In FIG. 7, rate is plotted vertically and time horizontally. The distance between successive horizontal dots represents one minute. The light curve presents the heart rate of the host. The heavy curve traced between the dots presents the corresponding pacemaker rate. The correlation between the heart rate and pacemaker rate was computed at between 0.6 and 0.8 for the part of the tape shown in FIG. 7. The correlation is not expected to be high because the host could only move her left arm (because of the surgery for the implantation) and was supine rather than on her feet.

Modifications and Equivalents

For the purposes of this invention, signals derived on the basis of physiological factors other than the myopotential (and this includes signals such as those derived from respiration rate, blood temperature and blood chemistry), as disclosed in the prior art, are not be considered equivalents of this invention. Typically the prior art teaches, in the Krasner et al. U.S. Pat. No. 3,593,718, the general concept of a variable-rate pacemaker that responds to the physiological factors of the host, giving respiration rate as an example. What has not been obvious from the prior art is to use the usually disregarded factor of myopotential which is always suppressed in accordance with prior-art teaching, thereby obtaining advantages in terms of having a system that does not rely upon moving parts and does not require any particular elaborate sensing means including a separate electrode, such as may be necessary in reliance on such other parameters as nerve signals, blood temperature or blood chemistry. Reliance upon the hitherto disregarded myopotential affords the opportunity for a particularly quick-responding yet relatively simple and inexpensive apparatus.

The application of this invention to an artificial heart is regarded as within the scope of equivalents of this invention.

It is also within the scope of equivalents of the invention to utilize a system wherein the computer microprocessor is responsive to more than one input in its determination of the pulse rate which is to be established and/or maintained. For example, the microprocessor may also be so programmed as to receive, from time to time, signals through its r-f input link such that the host may, within limits, adjust the output pulse rate upward or downward. If, for example, the existing programming has caused the pulse rate to be diminished somewhat too rapidly after certain exertions by the host, leaving him or her with such a feeling of shortness of breath (dyspnea) as would indicate the advisability of having an increased circulation of blood, a higher pulse rate for some period of time, it is within the scope of equivalents of this invention, when myopotential signals are being used as a predominant basis for determining the output pulse rate, to have the pulse rate modified upwardly by having the host press a button on an external programmer means with which the host may be provided. However, such practice is subject to close scrutiny by, and approval of, the physician of the host. It is also within the scope of equivalent of this invention, in such a case, to have the microprocessor means 31 include programming such that it "learns", from its experiences with requests for greater or lesser circulation, to use a slower or faster rate of return to the "steady" or "inactive" state.

While preferred embodiments of this invention have been disclosed herein, many modifications thereof are feasible. This invention is not to be restricted except insofar as is necessitated by the spirit of the prior art.

We claim:

1. A heart pacemaker which in operation accommodates the physical activity of the host in whom said pacemaker is implanted; said pacemaker including pulse-generating means, means for conditioning said pulse-generating means to produce heart-stimulating pulses at predetermined intervals, means, connected to said conditioning means, for impressing said heart-stimulating pulses on the heart of the host, means connected to said conditioning means, for impressing on said conditioning means, myopotential pulses generated as a result of the physical activity of the host and means, responsive to said impressed myopotential pulses, for varying said predetermined intervals in dependence upon said physical activity to accommodate the length of said intervals to said physical activity.

2. The pacemaker of claim 1 wherein the conditioning means includes timing means for subdividing each predetermined interval between pulses conditioned by the conditioning means into a refractory subinterval during which the impressing of a pulse on the heart of the host is suppressed, followed by an escape subinterval during which the impressing of a pulse is enabled, said refractory subinterval being initiated by the impressing of a pulse on the heart, the varying means varying the duration of the escape subinterval.

3. A heart pacemaker which in operation accommodates the physical activity of the host in whom said pacemaker is implanted as manifested by myopotential voltage-value signals resulting from the physical activity derived from the body of said host; said pacemaker including
    (a) an electrode to engage the heart of said host,
    (b) pulse-generating means and
    (c) means, including timing means, for conditioning said pulse-generating means to generate heart-stimulating pulses at pacing cycle intervals of predetermined duration,
    (d) a first channel means, connected to said electrode and to said pulse-generating means and to said conditioning means, for transmitting only pulses generated in the heart of the host to said conditioning means and, in the absence of a pulse generated in the heart prior to the end of an interval timed by said timing means, a second channel means for transmitting pulses generated by said pulse-generating means to said heart said timing means establishing a refractory interval following each pulse, whether generated by the heart or by said conditioning means during which pulses generated by the heart during the refractory interval are suppressed, said timing means also establishing a sampling interval during said refractory interval,
    (e) an additional channel means connected to said electrode and to said timing means for transmitting during each said sampling interval, myopotential signals generated as a result of physical activity of the host to said timing means, and
    (f) means, connected to said timing means, for varying the duration of said pacing cycle intervals in dependence upon said myopotential signals to accommodate said duration to said physical activity of said host.

4. The pacemaker of claim 3 characterized by that the additional channel means has threshold means enabling the transmission only of myopotential signals having an amplitude exceeding a predetermined magnitude.

5. The pacemaker of claim 3 characterized by a pacemaker having an electrically conductive casing, and further characterized by that the additional channel means includes means, connected to the electrode and the casing, for deriving the myopotential signals transmitted to the timing means.

6. The pacemaker of claim 3 wherein the threshold of the first channel means is about three millivolts and the threshold of the additional channel is about one-half millivolt.

7. As an article of manufacture, a pacemaker to be implanted in a host, said pacemaker including means, to be physically connected to the heart of said host, when conditioned for stimulating heart contractions of said host, the said stimulating means also including means electrically connected to said physically-connected means, for maintaining the stimulation of the heart of said host at a rate always remaining within predetermined limits, and also actuable for increasing or decreasing said rate while said rate remains between said limits, and means, connected to said physically-connected means and to said electrically-connected means, for actuating said electrically-connected means to increase or decrease said rate predominantly in accordance with the respective presence or absence of myopotential signals that are generated by physical activity of said host, said actuable means when actuated accommodating said rate to said physical activity of said host.

8. An article as defined in claim 7, wherein the stimulating means including the maintaining means has no moving parts.

9. An article as defined in claim 7, wherein the actuating means includes means for detecting the frequency of myopotential signals having an amplitude exceeding a predetermined threshold magnitude and in the presence of such myopotential signals for actuating the maintaining means to increase the rate of stimulating heart contractions by said maintaining means responsive to such detected signals, the increase having a magnitude dependent on said frequency.

10. An article as defined in claim 9, wherein the maintaining means has no moving parts.

11. The method of accommodating a heart pacemaker to the physical activity of the host in whom said pacemaker is implanted; said method comprising: conditioning said pacemaker to generate successive heart-stimulating pulses at intervals, sensing the myopotential signals resulting from the physical activity of the host, and, responsive to said myopotential signals, conditioning the pacemaker to modify the generation of said successive heart-stimulating pulses so that said heart-stimulating pulses are produced at intervals whose duration accommodates the physical activity of the host.

12. The method of claim 11 including sensing by the pacemaker of heart-stimulating pulses and immediately following a heart-stimulating pulse disabling the pacemaker during a refractory subinterval from sensing heart-stimulation pulses, and immediately following said refractory subinterval enabling said pacemaker to sense heart-stimulating pulses during an escape subinterval and modifying the generation of successive heart-stimulating pulses responsive to the myopotential signals to vary the duration of the total interval equal to the refractory subinterval plus the escape subinterval by changing the duration of the escape subinterval in dependence upon the myopotential signals.

13. The method of claim 12 including the step of sensing the myopotential signals sensing during a sensing sampling interval.

14. The method of claim 13 including the steps of counting the myopotential pulses sensed during the sampling interval, and if said number exceeds a predetermined threshold number, setting the duration between the conditioning of successive heart-stimulating pulses in dependence upon the said number of myopotential pulses sensed during the sampling interval.

15. The method of claim 13 including the steps of determining the average of the amplitudes of the myopotential pulses sensed during the sampling interval and setting the duration between the conditioning of successive heart-stimulating pulses in dependence upon the magnitude by which the said average of the amplitude of the myopotential pulses sensed during said sampling interval exceeds a threshold amplitude.

16. The method of claim 13 including the steps of determining the sum of the amplitude of the myopotential pulses sensed during the sampling interval, and setting the duration between the conditioning of successive heart-stimulating pulses in dependence upon the magnitude by which said sum of the amplitudes of myopotential pulses sensed during the sampling interval exceeds a predetermined threshold amplitude.

17. The method of claim 13 including the steps of determining the average of the number of myopotential pulses sensed during a predetermined number of successive sampling intervals, and setting the duration between the conditioning of successive heart-stimulating pulses in dependence upon said average of the numbers of myopotential pulses sensed during said predetermined number of successive sampling intervals.

18. The method of claim 12 including the step of sensing the myopotential signal during a sampling subinterval which occurs during the refractory subinterval.

19. The method of claim 18 including the step of sampling the myopotential signal during a sampling subinterval which occurs during the refractory subinterval just prior to the start of the escape subinterval.

20. The method of claim 12 wherein the pacemaker includes a computer characterized by the steps of: entering in the computer the duration of the escape subinterval during each heart-stimulating interval as a first number, entering in said computer a second number representing a measurement of myopotential signal activity occurring during heart stimulating intervals succeeding said each heart stimulating interval, and conditioning the pacemaker during said succeeding intervals to generate successive heart-stimulating pulses at intervals whose duration is dependent upon said measurement of myopotential signals by setting the duration of the escape subinterval during said successive heart-stimulating intervals substantially equal to the first number less the second number.

* * * * *